United States Patent [19]

Hussain

[11] Patent Number: 5,008,477

[45] Date of Patent: Apr. 16, 1991

[54] DECABROMODIPHENYL ALKANE PROCESS

[75] Inventor: Saadat Hussain, Baton Rouge, La.

[73] Assignee: Ethyl Corporation, Richmond, Va.

[21] Appl. No.: 492,756

[22] Filed: Mar. 14, 1990

[51] Int. Cl.$^5$ .................. C07C 17/12; C07C 25/18
[52] U.S. Cl. .................... 570/208; 570/206; 570/210; 570/211; 252/601
[58] Field of Search ............... 570/206, 208, 210, 211

[56] References Cited

U.S. PATENT DOCUMENTS 3,752,856  8/1973  Macy et al. ..................... 570/206
3,763,248  10/1973  Mitchell ........................ 570/206

FOREIGN PATENT DOCUMENTS 1411524  10/1975  United Kingdom ............... 570/206

*Primary Examiner*—Werren B. Lone
*Attorney, Agent, or Firm*—E. E. Spielman, Jr.; David E. LaRose

[57] ABSTRACT

This invention relates to a process for preparing a white or at least near white product which is predominant in decabromodiphenyl alkane and which has an average bromine number of at least 9.0.

18 Claims, No Drawings

DECABROMODIPHENYL ALKANE PROCESS

BACKGROUND OF THE INVENTION

This invention relates to a process for preparing a product predominant in decabromodiphenyl alkane.

Polybromodiphenyl alkanes, e.g. decabromodiphenyl ethane, are known flame retardants for use in polyolefin and in polystyrenic-based formulations. On a commercial basis, the polybromodiphenylalkane would be supplied to the formulation as a product predominant in the polybromodiphenyl alkane selected. The product would have a form and an impurity content which would be characteristic of the process used to produce it. If the product's physical characteristics, e.g. thermal stability, limit the formulation's processability, then the processor's desire for the product is limited at best. If the product's color is not white or at least near white, the product will be suitable for use in some formulations, however, the product's use may not be acceptable in formulations calling for a white or light color.

THE INVENTION

The process of this invention yields a white or near white product which is predominant in decabromodiphenyl alkane and has an average bromine number of at least 9.0. The process comprises: forming a stirrable reaction mass by feeding molten diphenylalkane to a reaction vessel to which a bromination catalyst and elemental bromine ($Br_2$) had been previously charged, the molten diphenylalkane being maintained under a non-oxidizing atmosphere prior to the feeding, and the bromine (i) containing about 10 ppm or less impurities, and (ii) being charged in an amount which provides from about 18 to about 30 moles of bromine per mole of diphenylalkane fed; maintaining the reaction mass at a temperature which is less than or equal to about 15° C. during the feeding; subsequent to the feeding, obtaining a reaction mass temperature within the range of from about 50° C. to about 60° C.; and recovering from the reaction mass the decabromodiphenyl alkane predominant product.

The diphenylalkane portion of the feed solution can be represented by the formula:

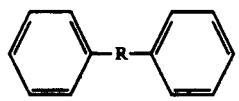

wherein R is an alkylene group containing 1 to 10 carbon atoms. Preferred R groups are methylene and ethylene which give, respectively, the preferred reactants, diphenylmethane and 1,2-diphenylethane. Exemplary of other diphenylalkanes are: 1-methyl-1,2-diphenylethane, 1,4-diphenylbutane, 1,6-diphenylhexane, 2,3-dimethyl-1,4-diphenylbutane, 2-ethyl-3-methyl-1,4-diphenylbutane, 2-methyl-1,7- diphenylhexane, 1,9-diphenylnonane and 1,10-diphenyldecane. The diphenylalkane reactant can be produced by various routes. For example, CA 97 38651d (Japanese Kokai 82/45114) and CA 46 7084g disclose the reaction of benzene and ethylene dihalide in the presence of aluminum trichloride to yield diphenyl alkane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often give the final decabromodiphenyl alkane product an off color. Exemplary of these color-causing impurities are diphenylmethane, and the methyl and ethyl derivatives of 1,2-diphenylethane. Diminishing the impurity content can be accomplished in a conventional manner, for example, the diphenylalkane can be recrystallized. See Example VII wherein a recrystallization method is described.

The diphenylalkane is fed to the reaction vessel in a molten state. Thus, the diphenylalkane is at a temperature above its melting point but not so high that it experiences degradation. For diphenylethane, the melting point is about 53° C. to 55° C. and, hence, the diphenyl ethane is preferably fed at a temperature of from about 55° C. to about 80° C. The higher temperatures are preferred as the viscosity of the molten diphenyl ethane can be lower thus making its feed to the reaction vessel more convenient. Most preferred is a temperature within the range of from about 70° C. to about 80° C.

It is a feature of this invention that the molten diphenylalkane be in a non-oxidizing atmosphere until it is fed into the reaction vessel. Such an atmosphere can be provided by most inert gases. For example, nitrogen, argon, neon, helium, krypton, xenon, and the like. By providing the inert atmosphere, it has been found that the color characteristics of the product are benefited. It is theorized that this benefit is a result of preventing or reducing the production of oxidation decomposition impurities in the molten diphenylalkane feed. The decomposition impurities are probably 1-hydroxy-1,2-diphenylethane, benzaldehydes, benzyl alcohols and the like. Such impurities apparently do impact the color characteristics of the product as can be seen by comparing Examples II and III hereof.

It has also been found that the bromine utilized in the process of this invention should contain 10 ppm or less organic impurities, e.g. oil, grease, carbonyl containing hydrocarbons, iron and the like, so that there is little, if any, impact on the color attributes of the product. Commercial grade bromine having such purity may be available. If such is not available, the organic impurities and water content of the bromine can be conveniently reduced by mixing together a 3 to 1 volume ratio of bromine and concentrated (94–98 percent) sulfuric acid. A two phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

The bromination catalyst used in the process of this invention is preferably $AlCl_3$ and/or $AlBr_3$, although use may be made of aluminum powder, iron powder, $FeCl_3$ and $FeBr_3$, alone or in combination with the aluminum trihalide(s). Other bromination catalysts are suitable, provided that they have sufficient catalytic activity to provide for the extent of bromination called for under the process conditions which will be encountered. Catalytic quantities are used. Typically, the catalysts will be present in an amount within the range of about 0.1 to about 20 weight percent, based on the weight of the diphenylalkane reactant used in the process. A preferred amount is within the range of from about 8 to about 15 weight percent on the same basis, with from about 9.0 to about 11.0 weight percent being most preferred.

The bromination catalyst and bromine can be charged to the reaction vessel in any order or together. It is preferred that both be cooled prior to their charging so that they will form a mix which is at least near the temperature at which the reaction mass will be maintained during the diphenylalkane addition. While the foregoing is a preferred technique, it is possible, though maybe not as convenient, for the catalyst and bromine, prior to charging, to be at temperatures other than the diphenylalkane addition temperature. If, prior to charging, the catalyst and bromine temperatures are above the addition temperature, the temperature of the resultant mix in the reaction vessel can be lowered to obtain the desired addition temperature. However, care should be taken not to aspirate atmospheric moisture into the reaction vessel during such lowering. The presence of moisture in the reaction vessel is detrimental as many bromination catalysts are deactivated by contact with water.

The amount of elemental bromine ($Br_2$) charged to the reaction vessel should provide sufficient bromine to effect the degree of bromination sought and to provide an easily stirred reaction mass. Generally, from about 18 to about 30 moles of bromine per mole of diphenylalkane feed will be suitable. Preferably from about 20 to about 28 moles of bromine per mole of diphenylalkane are used. A most preferred amount is in the range of from about 23 to 27 moles of bromine per mole of diphenylalkane. After the reaction is complete, the bromine not used in the ar-substitution will be a liquid component of the reaction mass and will continue to serve the before-mentioned purpose of providing a stirrable reaction mass.

The diphenylalkane addition generally occurs over a period of time and the addition rate is dependent upon the scale of the reaction and the ability to control the temperature and to handle hydrogen bromide evolution. On a laboratory scale, the addition typically requires about 0.5 to about 1.5 hours while on a commercial scale, the addition could involve about 1.0 to about 10.0 hours or longer. Four to five hours would be typical for the commercial scale.

During the diphenylalkane addition, the reaction mass temperature is kept below about 15° C., and preferably within the range of from 0° C. to about 15° C. Since the bromination of diphenylalkane is exothermic, cooling of the reaction mass will be needed to obtain the addition temperature as required above. The heat of reaction can be removed from the reaction mass by cooling the reaction vessel or by having the reaction mass under reflux conditions so that heat can be removed by the use of an overhead condenser. The rate of diphenylalkane addition will be dependent upon the ability of the equipment to maintain the selected addition temperature.

After the addition is at least substantially complete, the reaction mass is brought to a temperature within the range of from about 50° C. to about 60° C. The temperature selected can provide a refluxing condition for the reaction mass, however, a refluxing condition is not necessary. The reaction mass is preferably kept at the selected temperature for that ride time which is needed to obtain an average bromine number of at least about 9.0. The average bromine number is defined as the average number of bromine atoms ar-substituted on each brominated diphenylalkane molecule in the product. Thus, an average bromine number of 9.0 indicates that not all of the diphenylalkane molecules in the product have been ring perbrominated, hence, the presence of the lower bromo homologs, e.g. nonobromodiphenyl alkane, octabromodiphenyl alkane, etc., in the product. As the average bromine number approaches 10.0, the amount of these lower bromo homologs will decrease and the amount of the decabromo homolog will increase.

To obtain the selected average bromine number above 9.0, sampling and analysis of the product, as it is produced, can be used to determine the sufficiency of the ride time. If a substantially perbrominated product is desired, the ride time is conveniently determined by monitoring the HBr evolution from the reaction mass. When the HBr evolution ceases to be detected, no further significant bromination is occurring and thus the ride time has been satisfied. Generally, the ride time will be from about 2 to about 5 hours, with 3 to 4 hours being preferred.

After the ride time, the reaction mass will comprise a liquid-solid mixture. The solid comprises brominated diphenylalkane, catalyst, entrained bromine and other impurities. The liquid will comprise mostly bromine. The recovery of the brominated diphenylalkane product and its entrained bromine is effected conventionally. For example, the reaction mass can be steam stripped to remove non-entrained bromine from the reaction mass and to deactivate the catalyst. The remaining solids are then washed with an aqueous base, e.g. an aqueous solution of NaOH or $Na_2CO_3$, to neutralize and remove any HBr present. A final water washing step is used to obtain a product which is predominate, i.e., 50+ weight percent, in decabromodiphenyl alkane. This product is of good color and can be further treated to have superior color. A preferred product is one which contains 95+ weight percent, and most preferable 98+ weight percent, decabromodiphenyl alkane.

The further treatment will generally include the removal of entrained bromine from the product. This removal can be effected by oven-aging the product at a temperature within the range of from about 230° C. to about 250° C. for 6 to 20 hours. Another method comprises heating the product to a temperature above about 70° C. and subsequently fracturing the hot product particles thereby releasing any entrained bromine therefrom. The fracturing can be accomplished by grinding, impacting, etc. the product particles.

The decabromodiphenyl alkane predominant product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to those skilled in the art that for all cases no single precise value for the proportion of the product in the formulation can be given, since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 wt. percent, preferably 10 to 30 weight percent, of the product when it is the only flame retardant compound in the formulation.

It is especially advantageous to use the product with an inorganic compound, especially ferric oxide, zinc oxide, zinc borate, the oxide of a Group V element, for example, bismuth, arsenic, phosphorus and especially antimony, in the formulation. Of these compounds, antimony oxide is especially preferred. If such a compound is present in the formulation, the quantity of product needed to achieve a given flame-retardancy is accordingly reduced. Generally, the product and the inorganic compound are in a weight ratio of from about 1:1 to about 7:1, and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidants, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

The following Examples merely illustrate the invention described herein and are not to be taken as limiting such inventions.

EXAMPLE I

The example is presented for comparative purposes. The $Br_2$ used was not purified prior to use in the procedure. The diphenylethane reactant was melted and added to the kettle under an ambient atmosphere. The diphenylethane reactant was obtained from Aldrich Chemical Company, Inc. and was recrystallized to enhance its purity.

A 500 mL resin kettle was equipped with a mechanical stirrer, a reflux condenser, a thermometer with a temperature regulator, an addition funnel wrapped with a heating tape, and a caustic scrubber. The kettle was charged with bromine (400.0 g, 2.5 moles), and cooled to 10° C., using an ice-bath. Anhydrous aluminum chloride (2.1 g) was then added to the kettle. Diphenylethane (18.2 g, 0.1 moles) was melted in the addition funnel to about 80° C. The molten diphenylethane was then added to the kettle in which the contents were at 10°-17° C. The addition took about 17 minutes. The kettle contents were heated to reflux (59° C.) for 3.5 hours. After refluxing, the kettle contents were cooled to 45° C. and water (200 mL) was added thereto. The kettle contents were allowed to come to room temperature. The kettle contents were then heated and distilled to remove the excess bromine. After bromine removal, the kettle contents were filtered to recover a solid product which was washed with water, and then with 10 percent aqueous HCl, followed by water again (2×200 mL). The washed product was heated in a forced-air oven at 200° C. for 22 hours. The heated product (94.0 g, 96.7 percent yield) had a melting point of 350°-356° C. and Hunter color values of L=84.7, a=0.95, b=10.12 and Y.I.=20.9.

EXAMPLE II

This example is presented for comparative purposes. The bromine used was not purified and the diphenyl ethane was melted and added to the kettle in the presence of air.

A 3-liter resin kettle was equipped with a mechanical stirrer, a thermometer with a therm-o-watch, an addition funnel wrapped with a heating tape, a heating mantel and double reflux condensers. The addition funnel was charged with ground diphenylethane (111.0 g, 0.60 moles), and heated slowly with the heating tape. The reactor was charged with bromine (2407.0 g, 15 moles) and catalyst ($AlCl_3$, 8.9 g). Molten diphenylethane (kept at 55°-66° C.) was then added to the bromine and catalyst over a period of 60-75 minutes. During the addition, the kettle temperature was kept at 25°-30° C. After the addition was complete, the reaction mixture was stirred and heated at reflux (60° C.) for 4.5 hours. Water (1000 mL) was then charged to the kettle and bromine was distilled off to a vaporhead temperature at 100° C. The product was filtered, washed once with water and then with xylene (250 mL). The product was oven-aged at 200° C. for 16 hours, to give 572.0 g (98 percent) of an off-white solid having Hunter color values of L=79.59, a=1.19, b=11.92 and Yellowness Index (Y.I.) of 28.15. The solid had a melting point of 340°-344° C. and a bromine content of 82.7 percent.

EXAMPLE III

This example illustrates a process of this invention. The equipment described in Example II was used for this example. The $Br_2$ used was purified by stirring together a mixture of bromine and concentrated $H_2SO_4$ (volume ratio of 3:1) for a period of about 12-14 hours. After the period, a two phase mixture is obtained with purified bromine comprising one of the phases. This bromine phase was recovered. Even though this recovered bromine was very pure, further purification was effected by distilling the bromine.

The kettle was charged with purified $Br_2$ (130 mL, 150 percent stoichiometric excess) and cooled to 15° C. Then $AlCl_3$ (1.8 g) was added and the kettle contents were stirred. To the kettle was then added diphenyl ethane (18.2 g, molten, under nitrogen). The kettle contents were kept between 10°-17° C. The diphenylethane addition occurred over 23 minutes. The kettle contents were then stirred for 30 minutes and allowed to warm. The kettle contents were then heated (with stirring) to 59° C. 3.5 hours. After this period, water (200 mL) was added and excess bromine was distilled from the kettle.

The kettle contents were then filtered to obtain a solid product which was washed with water (3×100 mL). The washed product was dried in air overnight. The dried product was then heated in a forced-air oven at 210° C. for 24 hours and then at 250° C. for 7 hours.

The product (93.6 g, 98 percent yield) had a melting point of 346°-354° C. and Hunter color values of L=84.06, a=1.05, b=7.8 percent and Y.I. 17.85.

EXAMPLE IV

The procedure of Example III was followed except that: (1) the kettle contents were brought to 50° C. after the diphenyl ethane addition was complete; (2) the washed product was dried at 100° C. for 30 minutes; and (3) the dried product was over-aged at 210° C. for 16 hours followed by heating at 240° C. for 3 hours.

The resultant product had a melting point of 347° C.-356° C. and Hunter color values of L=87.42, a=0.01, b =6.52 and Y.I.=13.78.

EXAMPLE V

The procedure of Example IV was followed except that the diphenylethane was only 98.8 percent pure.

The final product had Hunter color values of L=87.34, b=8.22 and Y.I.=17.06.

EXAMPLE VI

The procedure of Example IV was followed except that: (1) after the bromine was distilled from the kettle, 10 mL of 50 percent aqueous NaOH was added to the kettle (resultant pH=12); (2) 5 mL HCl was then added to adjust the pH to about 8; (3) 2.1 g of sodium gluconate was added and the kettle contents were stirred; (4) after the last addition, the resultant product was washed with water to obtain a pH of about 7; and (5) the product was then air dried and placed in a forced-air oven at 210° C. for 17 hours and then at 245° C. for 2.5 hours.

The final product had Hunter color values of L=86.64, a=0.41, b=6.64 and Y.I.=14.36.

EXAMPLE VII

The following example illustrates a method for purifying diphenylethane.

A 1-L beaker was charged with methanol (300 mL). Crude diphenylethane (300g) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5g (91.5%). The recrystallized material had a melting point of 50° C.-54° C. which is slightly higher than the 49° C.-50° C. for the original starting diphenylethane. The starting diphenylethane had a Y.I. of 33.2 (L=81.2, a=−2.9, b=16.1) while the recrystallized diphenylethane material had a Y.I. of 2.8. (L=90.8, a=−0.4, b=1.4).

What is claimed is:

1. A process for preparing a product predominate in decabromodiphenyl alkane, having an alkyl group bridging the aromatic rings, and having an average bromine number of at least 9.0, the process comprising: forming a stirrable reaction mass by feeding molten diphenylalkane to a reaction vessel to which a bromination catalyst and bromine had been previously charged, the molten diphenylalkane being maintained under a non-oxidizing atmosphere prior to the feeding, and the bromine (i) containing about 10 ppm or less impurities, and (ii) being charged in an amount which provides from about 18 to about 30 moles of bromine per mole of diphenylalkane fed; maintaining the reaction mass at a temperature which is less than or equal to about 15° C. during the feeding; subsequent to the feeding, obtaining a reaction mass temperature within the range of from about 50° C. to about 60° C.; and recovering from the reaction mass the decabromodiphenyl alkane predominant product, wherein the alkyl group contains 1 to 10 carbon atoms.

2. The process of claim 1 wherein the diphenylalkane reactant is diphenylethane.

3. The process of claim 1 wherein the product comprises 95$^{30}$ weight percent decabromodiphenyl alkane.

4. The process of claim 3 wherein the decabromodiphenyl alkane is decabromodiphenyl ethane.

5. The process of claim 1 wherein the amount of bromine charged provides from about 20 to about 28 moles of bromine per mole of diphenylalkane.

6. The process of claim 1 wherein the amount of bromine charged provides from about 23 to about 27 moles of bromine per mole of diphenylalkane.

7. The process of claim 2 wherein the diphenylethane is at a temperature of from about 55° C. to about 80° C. when fed to the reaction vessel.

8. The process of claim 7 wherein the diphenylethane is fed under a nitrogen atmosphere.

9. The process of claim 1 wherein, during the diphenylalkane feed the reaction mass is at a temperature within the range of from about 0° C. to about 15° C.

10. The process of claim 1 wherein the reaction mass temperature which is obtained subsequent to the diphenylalkane feed is maintained from about 2 to about 5 hours.

11. The process of claim 1 wherein the product is recovered by steam stripping the reaction mass to remove non-entrained bromine therefrom.

12. The process of claim 11 wherein the recovered product is washed with an aqueous base to neutralize any HBr which may be present.

13. The process of claim 12 wherein the washed product is treated with a chelating agent to facilitate the removal of any deactivated catalyst therefrom.

14. The process of claim 13 wherein the treated product is washed with an aqueous medium.

15. The process of claim 14 wherein the aqueous medium washed product contains that 95+ weight percent decabromodiphenyl alkane.

16. The process of claim 14 wherein the aqueous medium washed product is further treated to remove entrained bromine therefrom.

17. The process of claim 14 wherein the aqueous medium washed product is heated to a temperature above about 70° C. and then fractured to release entrained bromine therefrom.

18. A flame retardant product predominant in decabromodiphenyl alkane, having an alkyl group bridging the aromatic rings, having an average bromine number of at least about 9.0 and having a Yellowness Index (ASTM E 323) between about 11.0 and about 18, wherein the alkyl group contains 1 to 10 carbon atoms.

* * * * *

UNITED STATES PATENT AND TRADEMARK OFFICE
CERTIFICATE OF CORRECTION

PATENT NO.   : 5,008,477
DATED        : April 16, 1991
INVENTOR(S)  : Saadat Hussain It is certified that error appears in the above-identified patent and that said Letters Patent is hereby corrected as shown below:

On the title page, under item [56]:
First reference cited reads "Macy et al." and should read -- Nacy et al. --.

Column 8, line 17 reads "comprises $95^{30}$ weight" and should read -- comprises $95^+$ weight --.

Signed and Sealed this

Seventeenth Day of November, 1992

Attest:

DOUGLAS B. COMER

Attesting Officer

Acting Commissioner of Patents and Trademarks